United States Patent
Ichikawa et al.

(10) Patent No.: US 6,908,982 B2
(45) Date of Patent: Jun. 21, 2005

(54) AMINO COMPOSITION AND PROCESS FOR PRODUCING THE SAME

(75) Inventors: Tetsushi Ichikawa, Hiratsuka (JP);
Hisayuki Kuwahara, Hiratsuka (JP);
Masatoshi Echigo, Hiratsuka (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 176 days.

(21) Appl. No.: 10/463,594

(22) Filed: Jun. 18, 2003

(65) Prior Publication Data

US 2004/0044176 A1 Mar. 4, 2004

(30) Foreign Application Priority Data

Jun. 18, 2002 (JP) ........................................ 2002-176977
Jun. 18, 2002 (JP) ........................................ 2002-176980

(51) Int. Cl.[7] .......................... C08L 63/00; C08G 59/50; C07C 211/00
(52) U.S. Cl. ........................ 528/124; 528/119; 528/120; 528/121; 528/122; 528/123; 528/418; 528/421; 564/336; 564/384; 564/388
(58) Field of Search ................................. 528/119, 120, 528/121, 122, 123, 124, 418, 421, 422; 564/1, 305, 306, 336, 384, 388

(56) References Cited

U.S. PATENT DOCUMENTS 4,034,040 A    7/1977  Cronin et al.
6,562,934 B2 *  5/2003  Yonehama et al. ......... 528/122
2002/0055605 A1  5/2002  Yonehama et al.

OTHER PUBLICATIONS

Database WPI, Section Ch., Week 197124 Derwent Publications Ltd., London, Great Britain: AN 1971–41876S XP002256787 & JP 46 021857 A (Showa Denko K K).

Patent Abstracts of Japan, vol. 1998, No. 06, Apr. 30, 1998 & JP 10 045878 A (Fuji Kasei Kogyo KK), Feb. 17, 1998.

* cited by examiner

*Primary Examiner*—Michael J. Feely
(74) *Attorney, Agent, or Firm*—Wenderoth, Lind & Ponack, L.L.P.

(57) ABSTRACT

An object of the present invention is to provide an amino composition which provides, when used as a curing agent for epoxy resin, a long pot life and an excellent appearance of a coating film to an epoxy resin composition without deteriorating the reactivity of the composition. The amino composition is obtained by addition reaction of diamine such as metaxylylenediamine and 1,3-bis(aminomethyl)cyclohexane and styrene, wherein the content of the diamine is less than 15% by weight based upon the total weight of the amino composition and the content of 1-addition product of having one phenethyl group is 50 to 100% by weight based upon the total weight of amino compound(s) obtained by the addition reaction.

18 Claims, No Drawings

AMINO COMPOSITION AND PROCESS FOR PRODUCING THE SAME

BACKGROUND OF THE INVENTION

1) Field of the Invention

The present invention relates to an amino composition containing a certain amino compound as a main component, a process for producing the same and the use thereof. The amino composition, when it is used as a curing agent for epoxy resin, provides a long pot life and an excellent appearance of a coating film to an epoxy resin composition without deteriorating its reactivity. Therefore, this amino composition is applicable to a curing agent for epoxy resin and a raw material thereof to be utilized in the field using epoxy resin including use as a coating material, use as a material for civil engineering and construction, use as an adhesive, use as a material for electricity and electronics, and use as a composite material. Further, this amino composition is applicable to a chain extender for polyurethane resin and a raw material thereof to be utilized in a field using polyurethane resin including use as foam, elastomer, coating adhesive, fiber, heather and water proof material.

2) Related Art

It has widely known that various polyamino compounds are used as a curing agent for epoxy resin and a raw material for curing agent thereof or a chain extender for polyurethane resin and a raw material for chain extender thereof.

Room temperature curing epoxy resin composition using these curing agent for epoxy resin are particularly utilized widely in a field of coating material such as a corrosion-resistant paint for ship, bridge and land and marine iron structure, and a field of civil engineering and construction such as lining, reinforcement and repair of concrete structure, a flooring material of building, lining of water supplying facility and sewerage, pavior, and adhesive material.

Representative examples of the amino compounds are as follows: aliphatic polyamino compound such as ethylenediamine, diethylenetriamine, triethylenetetramine, tetraethylenepentamine, pentaethylenehexamine, hexamethylenediamine; aliphatic polyamino compound having aromatic ring such as xylylenediamine; alicyclic polyamino compound such as menthenediamine, isophoronediamine, bis(aminomethyl)cyclohexane, N-aminomethylpiperazine; aromatic polyamino compound such as phenylenediamine, diaminodiphenylmethane, diaminodiphenylsulfone; other polyamino compounds such as polyamino compound having polyether framework, polyamino compound having norbornane framework. These polyamino compounds have their own characteristic features respectively caused by the reactivity of their amino groups, namely their active hydrogen. Therefore, these polyamino compounds are used as a curing agent for epoxy resin directly or with suitable modification for each compound.

Particularly, a diamine represented by the formula (1) or a curing agent for epoxy resin using the diamine as a raw material have a feature that they are suitable for curing at relatively low temperature, since their reactivity with an epoxy resin is higher and the curing speed of an epoxy resin composition is faster than other polyamino compounds or a curing agent for epoxy resin using the same as a raw material. Further, they have features to provide an excellent curing property of an epoxy resin composition, an excellent performance of cured coating film of epoxy resin, an excellent physical property of an epoxy resin cured product and an excellent adhesion property of an epoxy resin cured product and the like. Especially, when used as a coating material, they have features to provide a coating film excellent in both gloss and leveling and a cured product excellent in both water resistance and chemical resistance.

However, on the other hand, an epoxy resin composition using a diamine represented by the formula (1) or a curing agent for epoxy resin using the diamine as a raw material has defects that it exhibits a short pot life and its workability is inferior when it is cured at room temperature. Further, it has defect that a performance of cured coating film of epoxy resin or a physical property and an adhesion property of an epoxy resin cured product occasionally deteriorates because such epoxy resin composition easily produces carbamate or carbonate by absorbing carbon dioxide or water vapor in the atmosphere. Particularly, it has defects that the appearance of a coating film tends to be inferior by the phenomena of whitening or stickiness.

SUMMARY OF THE INVENTION

In Japanese Patent Application No. 2001-269074, the inventors presented an amino compound obtained by addition reaction of a diamine represented by the formula (1) with an alkenyl compound and a process for producing the same, and disclosed that a long pot life is provided to an epoxy resin composition by using the amino compound as a curing agent for epoxy resin. However, it is desired to provide an epoxy resin composition having not only a long pot life but also an excellent reactivity and an excellent appearance of a cured product, especially an excellent appearance of a coating film in the case of using the composition as a coating material.

An object of the present invention is to provide an amino composition which provides, when used as a curing agent for epoxy resin, a long pot life and an excellent appearance of a coating film to an epoxy resin composition without deteriorating the reactivity of the composition, and a process for producing the same.

Another object of the present invention is to provide a curing agent for epoxy resin which provides an excellent performance of cured coating film of epoxy resin, an excellent physical property of an epoxy resin cured product and an excellent adhesion property of an epoxy resin cured product, to provide an epoxy resin composition containing the curing agent, and to provide an epoxy resin cured coating film and an epoxy resin cured product obtained by curing the epoxy resin composition, which are suitable for a use as a coating material and a material for civil engineering and construction.

As a result of extensive studies, the inventors have found that an amino composition obtained by addition reaction of the diamine represented by the formula (1) and styrene in which a particular amino compound that is an addition product out of several kinds of addition products having different number of addition molecules and different addition structure is comprised in the certain ratio and the content of the unreacted diamine represented by the formula (1) is below a certain amount provides a long pot life and an excellent appearance of a coating film to an epoxy resin composition without deteriorating the reactivity of the composition when it is used as a curing agent for epoxy resin, and further provides an excellent performance of cured coating film of epoxy resin, an excellent physical property of an epoxy resin cured product and an excellent adhesion property of an epoxy resin cured product and is suitable for a use as an epoxy resin coating material and a material for civil engineering and construction, and have accomplished the present invention.

That is, the present invention provides an amino composition described in the following 1)–2), a process for producing an amino composition described in 3), a curing agent for epoxy resin described in 4), an epoxy resin composition described in 5)–7), and an epoxy resin cured product described in 8).

1) An amino composition comprising at least one amino compound selected from the group of amino compounds represented by the following formula (2) as a main component, obtained by addition reaction of diamine represented by the following formula (1) and styrene, wherein the content of diamine represented by the following formula (1) is less than 15% by weight based upon the total weight of said amino composition and the content of amino compound represented by the formula (2) in which R1, R2, and R3 are all hydrogen is 50 to 100% by weight based upon the total weight of said amino compound(s) selected from the group of the amino compounds represented by the formula (2).

$$H_2N-H_2C-A-CH_2-NH_2 \quad (1)$$

wherein A is a phenylene group or a cyclohexylene group

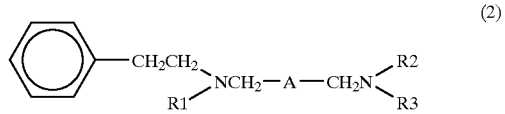

(2)

wherein A is a phenylene group or a cyclohexylene group, R1, R2, and R3 are, each independently, hydrogen or a phenethyl group.

2) The amino composition according to 1), wherein the content of diamine represented by the following formula (1) is less than 2% by weight based upon the total weight of said amino composition.

3) A process for producing an amino composition according to 1) or 2), which comprises performing addition reaction of diamine represented by the formula (1) and styrene, wherein the reaction mole ratio of styrene and diamine (styrene/diamine) is in the range of 0.25 to 1.75 and at least a part of unreacted diamine in the reaction mixture is removed by distillation or extraction.

4) A curing agent for epoxy resin comprising the amino composition according to 1) or 2).

5) An epoxy resin composition comprising an epoxy resin and the curing agent for epoxy resin according to 4).

6) The epoxy resin composition according to 5), wherein said composition is used as a coating material.

7) The epoxy resin composition according to 5), wherein said composition is used as a material for civil engineering and construction.

8) An epoxy resin cured product obtained by curing the epoxy resin composition according to 5) to 7).

DETAILED DESCRIPTION OF THE INVENTION

The amino composition of the present invention is obtained by addition reaction of the diamine represented by the formula (1) with styrene and comprises at least one amino compound selected from the group of amino compounds represented by the formula (2) as a main component.

The group of amino compounds represented by the formula (2) is consisted of an addition product wherein R1, R2, and R3 are all hydrogen (1-addition product), an addition product wherein any two of R1–R3 are hydrogen and one is a phenethyl group (2-addition product), an addition product wherein any two of R1–R3 are phenethyl groups and one is hydrogen (3-addition product), and an addition product wherein R1, R2, and R3 are all phenethyl groups (4-addition product). The amino compound(s) contained in the amino composition of the present invention is(are) selected from the above group of amino compounds.

Example of diamine represented by the formula (1) to be used in the present invention include orthoxylylenediamine, metaxylylenediamine, paraxylylenediamine, 1,2-bis(aminomethyl)cyclohexane, 1,3-bis(aminomethyl)cyclohexane, and 1,4-bis(aminomethyl)cyclohexane, among which metaxylylenediamine and 1,3-bis(aminomethyl)cyclohexane are particularly preferable. Each of them may be used individually or plural of them may be used.

Further, other polyamino compounds may be mixed to the diamine represented by the formula (1). However, when the amount of other polyamino compounds to be mixed is larger than the amount of diamine represented by the formula (1), the features of the amino composition of the present invention using diamine represented by the formula (1) to provide an epoxy resin cured coating film excellent in both gloss and leveling and to provide a cured product excellent in both water resistance and chemical resistance cannot be maintained. Therefore, it is preferable that the amount of other polyamino compounds is 1 part by weight or below per 1 part by weight of diamine represented by the formula (1).

Examples of other polyamino compound to be mixed with diamine represented by the formula (1) include aliphatic polyamines such as ethylenediamine, diethylenetriamine, triethylenetetramine, hexamethylenediamine and polyoxyalkylenepolyamine; alicyclic polyamines such as isophoronediamine, norbornanediamine, 1,4-diaminocyclohexane and di(aminohexyl)methane; aromatic polyamines such as metaphenylenediamine, diaminodiphenylmethane and diaminodiphenylsulfone and heterocycle polyamines such as N-aminoethylpiperazine and 3,9-bis(3-aminopropyl)-2,4,8,10-tetraoxaspiro[5,5]undecane.

As mentioned above, the amino compound of the present invention is a compound or the mixture of compounds selected from the group of the amino compounds represented by the formula (2). Since the amino composition of the present invention is obtained by addition reaction of the above-mentioned diamine and styrene, it usually is a mixture which contains unreacted diamine represented by the formula (1) and the like other than the amino compound(s) selected from the group of the amino compounds represented by the formula (2). The content of diamine represented by the formula (1) in the amino composition is less than 15% by weight, preferably less than 5% by weight, more preferably less than 2% by weight based upon the total weight of the amino composition. The lower limits of the content of diamine is not limited.

By keeping the content of diamine below 15% by weight in the amino composition, especially when an epoxy resin composition is prepared using the amino composition as a curing agent for epoxy resin, it is possible to prevent the epoxy resin composition from formation of carbamate or carbonate by absorbing carbon dioxide or water vapor in the atmosphere, to avoid the phenomena of whitening or stickiness of a coating film and to prevent the coating film from deteriorating of the appearance.

In the amino composition of the present invention, the content of the addition product wherein R1, R2, and R3 are all hydrogen (1-addition product) is 50 to 100% by weight, preferably 60 to 100% by weight based upon the total weight of the amino compound(s) selected from the group of the amino compounds represented by the formula (2).

When the amount of the 1-addition product is less than 50% by weight, the reactivity of the epoxy resin composition may easily deteriorate. The preferable higher limit of the proportion of 1-addition product based upon the total weight of the amino compound(s) selected from the group of the amino compounds represented by the formula (2) is not limited.

According to a process for producing an amino composition of the present invention, it is preferable to carry out addition reaction of diamine represented by the formula (1) and styrene by adjusting the reaction mole ratio of styrene and diamine (styrene/diamine) in the range of 0.25 to 1.75. Less than 0.25 of the reaction mole ratio is unfavorable because the content of unreacted diamine in the amino composition is increased and it becomes difficult to remove the unreacted diamine by extraction or it takes time to remove the unreacted diamine by distillation. More than 1.75 of the reaction mole ratio is unfavorable because the content of 1-addition product in which R1, R2, and R3 are all hydrogen easily becomes less than 50% by weight based upon the total weight of the amino compounds represented by the formula (2) and the reactivity of the epoxy resin composition may easily deteriorate.

Preferable catalyst to be used in the process of producing amino composition of present invention includes any substance exhibiting strong basicity. Examples of such catalyst include alkaline metal, alkaline metal amide and alkylated alkaline metal. Among them, alkaline metal amide by the general formula MNRR' wherein M is an alkaline metal, N is nitrogen and R and R' are, each independently, hydrogen or an alkyl group, is preferable and lithium amide (LiNH$_2$) is more preferable.

The amount of the catalyst depends on conditions such as species of raw material, reaction proportion and reaction temperature, and is usually 0.05 to 5% by weight and preferably 0.1 to 3% by weight based upon the total weight of raw material. When the amount of catalyst is below 0.05% by weight, the reaction rate may decrease, whereas above 5% by weight, the reaction rate does not increase which is not economical.

The reaction temperature is not limited on the condition that it is a melting point of diamine represented by the formula (1) or above. Usually, it is 25 to 150° C. and preferably 50 to 100° C. When the reaction temperature is below 25° C., the reaction rate of diamine represented by the formula (1) and styrene is slow, whereas above 150° C., since a polymer of styrene is produced as a by-product, it is desirable to select the reaction temperature depending on species of raw material, reaction proportion and species and amount of the catalyst.

The strong base catalyst such as alkaline metal amide readily reacts with moisture or carbon dioxide in air. Therefore, it is preferable to exclude the influence of moisture and carbon dioxide by carrying out the reaction in an inert gas such as nitrogen, helium or argon.

After the completion of the reaction, the reaction liquid thus obtained comprises amino compound(s) produced by the reaction and catalyst. The reaction liquid usually further contains unreacted diamine raw material and/or unreacted styrene. When alkaline metal amide is used as the catalyst, it is possible to change the alkaline metal amide to a readily removable salt thereof by adding acids such as hydrochloric acid, hydrogen chloride gas and acetic acid, alcohols such as methanol and ethanol or water, and then filtrate it. For example, when water is used, alkaline metal amide is changed to hydroxide thereof which is easy to filtrate.

The amino composition obtained after the reaction is completed and the precipitate such as used catalyst is removed usually contains unreacted diamine represented by the formula (1) as mentioned above. When the content of the unreacted diamine is 15% by weight or more, it is desirable to remove the diamine so that the content of the diamine become below 15% by weight, preferably below 5% by weight, more preferably 2% by weight.

The removal of the diamine can be carried out by distillation or extraction. Though the method of distillation is not limited, the removal is easily carried out by distillation under reduced pressure. In the case of extraction, solvent is not limited as long as the diamine is soluble and the group of amino compounds represented by the formula (2) is not solved to the solvent. The preferable solvent is Water.

The amino composition of the present invention has reactivity with an epoxy resin or isocyanate and is useful as a curing agent for epoxy resin and a chain extender for polyurethane resin. Particularly, when the amino composition is applied to a curing agent for epoxy resin, it provides a long pot life and an excellent appearance of a coating film to an epoxy resin composition without deteriorating the reactivity of the composition.

In the case of using the amino composition of the present invention as a curing agent for epoxy resin, the curing agent may be used alone or as a mixture with other polyamino curing agents for epoxy resin. Though the mixing ratio is not limited, it is preferable to select the ratio within limits not losing the characteristic of the amino composition of the present invention.

The epoxy resin composition containing the amino composition of the present invention as a curing agent for epoxy resin provides an excellent appearance of coating film and an excellent physical property of cured product. Therefore, it is especially useful as a coating material or a material for civil engineering and construction.

Examples of epoxy resin used for an epoxy resin composition useful as a coating material or a material for civil engineering and construction preferably include bisphenol A type epoxy resin and bisphenol F type epoxy resin which may be used alone or as a mixture with each other. However, usable epoxy resin is not limited and any epoxy resin having glycidyl group reactive with active hydrogen of the amino composition of the present invention containing the curing agent for epoxy resin can be used.

Though the content of the amino composition in an epoxy resin composition is not limited, it is preferable to mix 0.7 to 1.2 active hydrogen equivalent of the amino composition based upon the total epoxy equivalent of epoxy resin. Further, components for modification such as filler and plasticizer, components for adjusting fluidity such as diluent and thixotropic agent, and other ingredients such as pigment, leveling agent, and tackifier may be added to the epoxy resin composition of the present invention depending on the intended use.

PREFERRED EMBODIMENT OF THE INVENTION

The present invention will be described in more detail below, referring to Examples which are not intended to limit the scope of the present invention.

Evaluation of the property of an epoxy resin composition and a cured product thereof is carried out by the following method.

[Evaluation of Pot Life]

300 g of epoxy resin composition was put in a polypropylene cup of 500 ml. Keeping the cup under the conditions of 23° C. and 50% RH, the time required to reach the maximum exothermic temperature was measured.

[Evaluation of Curing Property]

Epoxy resin composition was coated on a glass plate (25×300×2 mm) with thickness of 76 micron under the conditions of 23° C. and 50% RH. The time required to reach each drying stage (set-to-touch, dust free, dry through) was measured by RCI drying meter of drying time. The shorter the time required is, the higher the curing property is.

[Evaluation of Appearance of Coating Film]

Epoxy resin composition was coated on a steel plate with thickness of 200 micron under the conditions of 23° C. and 50% RH. After 7 days of curing, the appearance of coating film such as whitening and stickiness was observed.

[Evaluation of Property of Cured Coating Film]

Epoxy resin composition was coated on a steel plate with thickness of 200 micron under the conditions of 23° C. and 50% RH. Intercoat Adhesion is evaluated with the coating film prepared by coating upper layer 1 day after coating lower layer.

a) Appearance:

The appearance of coating film after 7 days of curing is evaluated visually (gloss, clarity, leveling), and by touching with finger (drying characteristics).

b) Intercoat Adhesion:

The coating film after 1+7 days of curing is evaluated referring to X cut-tape method of JIS K 5400.

c) Water Resistance:

Water droplets were dropped on a coating film after 1, 4, and 7 days of curing. Change of the appearance of the coating film passed 1 day after dropping was evaluated visually.

d) Chemical Resistance:

Coated steel plate after 7 days of curing was dipped in each chemical (sodium hydroxide with the concentration of 10%, sulfuric acid with the concentration of 10%, acetic acid with the concentration of 10%, methanol, and toluene) for 7 days under the condition of 23° C. Change of the appearance of the coating film was evaluated visually. Salt spray test was carried out being compliant with JIS K 5400.

e) Evaluation:

Evaluation was carried out by the following 4 stages of criteria.

⊚; Excellent, ○; good Δ; fair x; poor

[Evaluation of Physical Property of Cured Product]

An epoxy resin composition was cured for 7 days under the conditions of 23° C. and 50% RH to prepare each test peace.

a) Tensile strength and tensile modulus of elasticity: compliant with JIS K 7113.
b) Flexural strength and flexural modulus of elasticity: compliant with JIS K 7171.
c) Compressive strength and compressive modulus of elasticity: compliant with JIS K 7181.

[Evaluation of Adhesion Property of Cured Product]

An epoxy resin composition was cured for 7 days under the conditions of 23° C. and 50% RH to prepare each test peace. With regard to the Flexural adhesion test under wet condition, an epoxy resin composition was cured for 7 days under the conditions of 23° C. and 85% RH to prepare each test peace.

a) Tensile shear adhesion strengh: compliant with JIS K 6850.
b) Flexural adhesion test: compliant with JIS A 6024.

EXAMPLE OF SYNTHESIS 1

953.4 g (7.0 mol) of metaxylylenediamine, manufactured by Mitsubishi Gas Chemical Co., Inc., in Japan (hereinafter, "MXDA") and 2.0 g (0.09 mol) of lithium amide, a reagent manufactured by Merck KGaA, were charged to a 2 L (liter) flask, equipped with an agitator, a thermometer, a nitrogen gas inlet, a dropping funnel and a condenser and its interior temperature was raised to 80° C. in a nitrogen gas stream with stirring. Keeping the temperature at 80° C., 364.7 g (3.5 mol) of styrene, special grade reagent, manufactured by Wako Pure Chemical Industries, Ltd., in Japan was added thereto dropwise over 1.5 hours. After the completion of dropwise addition, its interior temperature was maintained to 80° C. for one hour.

Then, after the reaction liquid was cooled to the room temperature, 16.2 g (0.9 mol) of water as the amount of 10 times equal mol to charged lithium amide was added thereto and stirred. After separating precipitates in the liquid in flask by filtration, remained water and unreacted MXDA were removed by vacuum distillation, whereby 703.3 g of amino composition A was obtained. The content of unreacted MXDA in the amino composition A was 1.1% by weight base upon the total weight of the amino composition. The content of addition product wherein R1, R2, and R3 are all hydrogen was 71% by weight based upon the total weight of the group of amino compounds represented by the formula (2).

EXAMPLE OF SYNTHESIS 2

817.2 g (6.0 mol) of MXDA and 2.9 g (0.13 mol) of lithium amide were charged to a flask similar as the one used in Example of Synthesis 1, and its interior temperature was raised to 80° C. in a nitrogen gas stream with stirring. Keeping the temperature at 80° C., 625.2 g (6.0 mol) of styrene was added thereto dropwise over 2 hours. After the completion of dropwise addition, its interior temperature was maintained to 80° C. for one hour.

Then, 618.2 g of distilled water of 80° C. was added. After stirring for 15 minutes, the reaction liquid was kept still for 5 minutes. The lower layer out of separated 2 layers of the liquid in flask was transferred to another flask. After repeating similar operation for 7 times, distilled water dissolved in the lower layer was removed by vacuum distillation, whereby 1117.3 g of amino composition B was obtained. The content of unreacted MXDA in the amino composition B was 0.7% by weight base upon the total weight of the amino composition. The content of addition product wherein R1, R2, and R3 are all hydrogen was 54% by weight based upon the total weight of the group of amino compounds represented by the formula (2).

EXAMPLE OF SYNTHESIS 3

845.0 g of amino composition B obtained by Example of Synthesis 2 was distilled under the conditions of temperature: 190–200° C., degree of vacuum: 2.8–3.0 mmHg, processing speed: 5.0–6.0 g/min using glass thin-film evaporator (MS-300 rotary membrane type) manufactured by Sibata Scientific technology Ltd., whereby 422 g of amino composition C was obtained. The viscosity of amino composition C was 52 mPa·s, amine value was 462, and the content of addition product wherein R1, R2, and R3 are all hydrogen was 95% by weight based upon the total weight of the group of amino compounds represented by the formula (2). The content of unreacted MXDA was below 0.1% by weight.

EXAMPLE OF SYNTHESIS 4

995.4 g (7.0 mol) of 1,3-bis(aminomethyl)cyclohexane, manufactured by Mitsubishi Gas Chemical Co., Inc., in Japan (hereinafter, "1,3-BAC") and 2.0 g (0.09 mol) of lithium amide were charged to a flask similar as the one used in Example of Synthesis 1, and its interior temperature was raised to 80° C. in a nitrogen gas stream with stirring. Keeping the temperature at 80° C., 364.7 g (3.5 mol) of styrene was added thereto dropwise over 1.5 hours. After the completion of dropwise addition, its interior temperature was maintained to 80° C. for one hour.

Then, after the reaction liquid was cooled to the room temperature, 16.2 g (0.9 mol) of water as the amount of 10 times equal mol to charged lithium amide was added thereto and stirred. After separating precipitates in the liquid in flask by filtration, remained water and unreacted 1,3-BAC were removed by vacuum distillation, whereby 700.7 g of amino composition D was obtained. The content of unreacted 1,3-BAC in the amino composition D was 1.2% by weight base upon the total weight of the amino composition. The content of addition product wherein R1, R2, and R3 are all hydrogen was 73% by weight based upon the total weight of the group of amino compounds represented by the formula (2).

EXAMPLE OF SYNTHESIS 5

853.2 g (6.0 mol) of 1,3-BAC and 3.0 g (0.13 mol) of lithium amide were charged to a flask similar as the one used in Example of Synthesis 1, and its interior temperature was raised to 80° C. in a nitrogen gas stream with stirring. Keeping the temperature at 80° C., 625.2 g (6.0 mol) of styrene was added thereto dropwise over 2 hours. After the completion of dropwise addition, its interior temperature was maintained to 80° C. for one hour.

Then, 645.2 g of distilled water of 80° C. was added. After stirring for 15 minutes, the reaction liquid was kept still for 5 minutes. The lower layer out of separated 2 layers of the liquid in flask was transferred to another flask. After repeating similar operation for 7 times, distilled water dissolved in the lower layer was removed by vacuum distillation, whereby 1126.2 g of amino composition E was obtained. The content of unreacted 1,3-BAC in the amino composition E was 0.6% by weight base upon the total weight of the amino composition. The content of addition product wherein R1, R2, and R3 are all hydrogen was 56% by weight based upon the total weight of the group of amino compounds represented by the formula (2).

EXAMPLE OF SYNTHESIS 6

1089.6 g (8.0 mol) of MXDA and 1.3 g (0.06 mol) of lithium amide were charged to a flask similar as the one used in Example of Synthesis 1, and its interior temperature was raised to 80° C. in a nitrogen gas stream with stirring. Keeping the temperature at 80° C., 208.4 g (2.0 mol) of styrene was added thereto dropwise over 1 hour. After the completion of dropwise addition, its interior temperature was maintained to 80° C. for one hour.

Then, after the reaction liquid was cooled to the room temperature, 10.8 g (0.6 mol) of water as the amount of 10 times equal mol to charged lithium amide was added thereto and stirred. After separating precipitates in the liquid in flask by filtration, remained water and unreacted MXDA were removed by vacuum distillation, whereby 447.8 g of amino composition F was obtained. The content of unreacted MXDA in the amino composition F was 2.5% by weight base upon the total weight of the amino composition. The content of addition product wherein R1, R2, and R3 are all hydrogen was 84% by weight based upon the total weight of the group of amino compounds represented by the formula (2).

EXAMPLE OF SYNTHESIS 7

544.8 g (4.0 mol) of MXDA and 3.8 g (0.17 mol) of lithium amide were charged to a flask similar as the one used in Example of Synthesis 1, and its interior temperature was raised to 80° C. in a nitrogen gas stream with stirring. Keeping the temperature at 80° C., 749.0 g (7.2 mol) of styrene was added thereto dropwise over 3 hours. After the completion of dropwise addition, its interior temperature was maintained to 80° C. for one hour.

Then, after the reaction liquid was cooled to the room temperature, 30.6 g (1.7 mol) of water as the amount of 10 times equal mol to charged lithium amide was added thereto and stirred. After separating precipitates in the liquid in flask by filtration, remained water was removed by vacuum distillation, whereby 1192.3 g of amino composition G was obtained. The content of unreacted MXDA in the amino composition G was 2.0% by weight base upon the total weight of the amino composition. The content of addition product wherein R1, R2, and R3 are all hydrogen was 28% by weight based upon the total weight of the group of amino compounds represented by the formula (2).

EXAMPLE OF SYNTHESIS 8

1137.6 g (8.0 mol) of 1,3-BAC and 1.3 g (0.06 mol) of lithium amide were charged to a flask similar as the one used in Example of Synthesis 1, and its interior temperature was raised to 80° C. in a nitrogen gas stream with stirring. Keeping the temperature at 80° C., 208.4 g (2.0 mol) of styrene was added thereto dropwise over 1 hour. After the completion of dropwise addition, its interior temperature was maintained to 80° C. for one hour.

Then, after the reaction liquid was cooled to the room temperature, 10.8 g (0.6 mol) of water as the amount of 10 times equal mol to charged lithium amide was added thereto and stirred. After separating precipitates in the liquid in flask by filtration, remained water and unreacted 1,3-BAC were removed by vacuum distillation, whereby 460.7 g of amino composition H was obtained. The content of unreacted 1,3-BAC in the amino composition H was 2.7% by weight base upon the total weight of the amino composition. The content of addition product wherein R1, R2, and R3 are all hydrogen was 82% by weight based upon the total weight of the group of amino compounds represented by the formula (2).

EXAMPLE OF SYNTHESIS 9

568.8 g (4.0 mol) of 1,3-BAC and 3.9 g (0.17 mol) of lithium amide were charged to a flask similar as the one used in Example of Synthesis 1, and its interior temperature was raised to 80° C. in a nitrogen gas stream with stirring. Keeping the temperature at 80° C., 749.0 g (7.2 mol) of styrene was added thereto dropwise over 3 hours. After the completion of dropwise addition, its interior temperature was maintained to 80° C. for one hour.

Then, after the reaction liquid was cooled to the room temperature, 30.6 g (1.7 mol) of water as the amount of 10 times equal mol to charged lithium amide was added thereto and stirred. After separating precipitates in the liquid in flask by filtration, remained water was removed by vacuum distillation, whereby 1227.3 g of amino composition I was obtained. The content of unreacted 1,3-BAC in the amino composition I was 2.6% by weight base upon the total weight of the amino composition. The content of addition product wherein R1, R2, and R3 are all hydrogen was 26% by weight based upon the total weight of the group of amino compounds represented by the formula (2).

EXAMPLE OF SYNTHESIS 10

817.2 g (6.0 mol) of MXDA and 2.9 g (0.13 mol) of lithium amide were charged to a flask similar as the one used in Example of Synthesis 1, and its interior temperature was raised to 80° C. in a nitrogen gas stream with stirring. Keeping the temperature at 80° C., 625.2 g (6.0 mol) of styrene was added thereto dropwise over 2 hours. After the completion of dropwise addition, its interior temperature was maintained to 80° C. for one hour.

Then, after the reaction liquid was cooled to the room temperature, 23.4 g (1.3 mol) of water as the amount of 10 times equal mol to charged lithium amide was added thereto and stirred. After separating precipitates in the liquid in flask by filtration, remained water was removed by vacuum distillation, whereby 1380.7 g of amino composition J was obtained. The content of unreacted MXDA in the amino composition J was 15.8% by weight base upon the total weight of the amino composition. The content of addition product wherein R1, R2, and R3 are all hydrogen was 55% by weight based upon the total weight of the group of amino compounds represented by the formula (2).

EXAMPLES 1 TO 5

Epoxy resin compositions were prepared by mixing bisphenol A type liquid epoxy resin with an epoxy equivalent of 190, manufactured by Japan Epoxy Resins Co., Ltd., trade name; Epicoat 828, and amino compositions A to E obtained by Examples of Synthesis 1 to 5 used as a curing agent for epoxy resin at a ratio shown in Table 1.

Pot life, the property of cured product and the appearance of epoxy resin coating film of the epoxy resin compositions thus obtained were evaluated. The evaluation result was shown in Table 1.

TABLE 1

|  | Example 1 | Example 2 | Example 3 | Example 4 | Example 5 |
|---|---|---|---|---|---|
| Epoxy resin composition (g) | | | | | |
| Epicoat 828 | 100 | 100 | 100 | 100 | 100 |
| Amino compound A | 48 | | | | |
| Amino compound B | | 55 | | | |
| Amino compound C | | | 42 | | |
| Amino compound D | | | | 51 | |
| Amino compound E | | | | | 59 |
| Pot life (min) | 280 | 340 | 191 | 225 | 290 |
| Curing property (hr:min) | | | | | |
| set-to-touch | 3:45 | 4:15 | 3:45 | 5:15 | 6:00 |
| dust free | 6:45 | 7:30 | 6:00 | 8:30 | 9:15 |
| dry through | 15:15 | 16:45 | 20:00 | 17:30 | 18:30 |
| Appearance | | | | | |
| whitening | not observed | not observed | not observed | not observed | not observed |
| stickiness | not observed | not observed | not observed | not observed | not observed |

EXAMPLES 6 TO 7, COMPARATIVE EXAMPLES 1 TO 3

Evaluation was carried out in the same manner as Examples 1 to 5 by using amino compositions F to J obtained by Examples of Synthesis 6 to 10 as a curing agent for epoxy resin. The evaluation result was shown in Table 2.

TABLE 2

|  | Example 6 | Comparative Example 1 | Example 7 | Comparative Example 2 | Comparative Example 3 |
|---|---|---|---|---|---|
| Epoxy resin composition (g) | | | | | |
| Epicoat 828 | 100 | 100 | 100 | 100 | 100 |
| Amino compound F | 44 | | | | |
| Amino compound G | | 75 | | | |
| Amino compound H | | | 45 | | |
| Amino compound I | | | | 76 | |
| Amino compound J | | | | | 42 |
| Pot life (min) | 175 | — | 130 | — | — |

TABLE 2-continued

|  | Example 6 | Comparative Example 1 | Example 7 | Comparative Example 2 | Comparative Example 3 |
|---|---|---|---|---|---|
| Curing property (hr:min) | | | | | |
| set-to-touch | 3:00 | 6:15 | 4:15 | 9:00 | 4:15 |
| dust free | 5:45 | 10:00 | 7:15 | 12:15 | 6:45 |
| dry through | 14:00 | >24:00 | 15:45 | >24:00 | >24:00 |
| Appearance | | | | | |
| whitening | observed | observed | not observed | not observed | not observed |
| stickiness | not observed | not observed | observed | observed | observed |

EXAMPLE OF SYNTHESIS 11

Unreacted MXDA was removed by vacuum distillation from 600 g of amino composition J obtained by the manner described in Example of Synthesis 10, whereby 486.4 g of Amino composition K was obtained. The content of unreacted MXDA in the amino composition K was 0.7% by weight base upon the total weight of the amino composition. The content of addition product wherein R1, R2, and R3 are all hydrogen was 55% by weight based upon the total weight of the group of amino compounds represented by the formula (2).

EXAMPLE OF SYNTHESIS 12

853.2 g (6.0 mol) of 1,3-BAC and 3.0 g (0.13 mol) of lithium amide were charged to a flask similar as the one used in Example of Synthesis 10, and its interior temperature was raised to 80° C. in a nitrogen gas stream with stirring. Keeping the temperature at 80° C., 625.2 g (6.0 mol) of styrene was added thereto dropwise over 2 hours. After the completion of dropwise addition, its interior temperature was maintained to 80° C. for one hour.

Then, after the reaction liquid was cooled to the room temperature, 23.4 g (1.3 mol) of water as the amount of 10 times equal mol to charged lithium amide was added thereto and stirred. After operating in the same manner as Example of Synthesis 10, 1409.3 g of amino composition L was obtained. The content of unreacted 1,3-BAC in the amino composition L was 17.2% by weight. The content of addition product wherein R1, R2, and R3 are all hydrogen was 56% by weight based upon the total weight of the group of amino compounds represented by the formula (2).

EXAMPLE OF SYNTHESIS 13

Unreacted 1,3-BAC was removed by vacuum distillation from 600 g of amino composition L obtained by Example of Synthesis 12, whereby 474.8 g of Amino composition M was obtained. The content of unreacted 1,3-BAC in the amino composition M was 0.6% by weight. The content of addition product wherein R1, R2, and R3 are all hydrogen was 55% by weight based upon the total weight of the group of amino compounds represented by the formula (2).

EXAMPLES 8 TO 9

Epoxy resin compositions were prepared by mixing bisphenol A type liquid epoxy resin with an epoxy equivalent of 190, manufactured by Japan Epoxy Resins Co., Ltd., trade name; Epicoat 828, and amino compositions K and M obtained by Examples of Synthesis 11 and 13 used as a curing agent for epoxy resin at a ratio shown in Table 3.

The epoxy resin compositions thus obtained were cured under the conditions of the temperature of 23° C. and 50% RH to prepare cured coating film and cured product with which evaluation of property was carried out.

TABLE 3

|  | Example 8 | Example 9 |
|---|---|---|
| Epoxy resin composition (g) | | |
| Epicoat 828 | 100 | 100 |
| Amino composition K | 55 | |
| Amino composition M | | 56 |
| Property of cured coating film | | |
| Appearance | | |
| Gloss | ◎ | ◎ |
| Clarity | ◎ | ◎ |
| Leveling | ○ | ○ |
| Drying characteristics | ◎ | ◎ |
| Intercoat adhesion | ◎ | ◎ |
| Water resistance (1/4/7 days) | ◎/◎/◎ | ◎/◎/◎ |
| Chemical resistance | | |
| 10% sodium hydroxide | ◎ | ◎ |
| 10% sulfuric acid | ◎ | ◎ |
| 10% acetic acid | ○ | ○ |
| methanol | ○ | ○ |
| toluene | ○ | ○ |
| solt spray test | ◎ | ◎ |
| Physical property of cured product | | |
| Tensile strength (Mpa) | 36.8 | 35.3 |
| Tensile modulus (Gpa) | 2.31 | 2.22 |
| Flexural strength (Mpa) | 69.4 | 70.1 |
| Flexural modulus (Gpa) | 2.05 | 2.31 |
| Compressive strength (Mpa) | 78.6 | 79.7 |
| Compressive modulus (Gpa) | 2.54 | 2.56 |
| Adhesion property of cured product | | |
| Tensile shear adhesion strength (Mpa) | 7.8 | 8.0 |
| Flexural adhesion strength | | |
| standard condition (Mpa) | 10.5 | 9.6 |
| wet condition (Mpa)*1 | 9.2 | 10.1 |

*1: Mortar block fracture was observed in all the test peaces.

As clear from the above Examples, amino composition obtained by addition reaction of diamine represented by the formula (1) with styrene, wherein the content of unreacted diamine represented by the formula (1) is less than a certain amount and the content of addition product represented by the formula (2) in which R1, R2 and R3 are all hydrogen is in the range of certain amount, particularly amino composition obtained by addition reaction of diamine represented by the formula (1) with styrene in a certain range of reaction ratio provides a long pot life and an excellent appearance of a coating film to an epoxy resin composition without deteriorating the reactivity of the composition when it is used as a curing agent for epoxy resin. Further, an epoxy resin composition using a curing agent for epoxy resin comprising an amino composition of the present invention provides an excellent performance of cured coating film of epoxy resin, an excellent physical property of an epoxy resin cured product and an excellent adhesion property of an epoxy resin cured product, and is suitable for use as epoxy resin coating material and use in the field of civil engineering and construction.

What is claimed is:

1. An amino composition comprising at least one amino compound selected from the group of amino compounds represented by the following formula (2) as a main component, obtained by addition reaction of diamine represented by the following formula (1) and styrene, wherein the content of diamine represented by the following formula (1) is less than 15% by weight based upon the total weight of said amino composition and the content of amino compound represented by the formula (2) in which R1, R2, and R3 are all hydrogen is 50 to 100% by weight based upon the total weight of said amino compound(s) selected from the group of the amino compounds represented by the formula (2).

$$H_2N-H_2C\text{-}A\text{-}CH_2-NH_2 \quad (1)$$

wherein A is a phenylene group or a cyclohexylene group

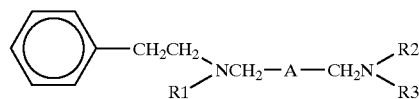
(2)

wherein A is a phenylene group or a cyclohexylene group.

R1, R2, and R3 are, each independently, hydrogen or a phenethyl group.

2. A process for producing an amino composition according to claim 1, which comprises performing addition reaction of diamine represented by the formula (1) and styrene, wherein the reaction mole ratio of styrene and diamine (styrene/diamine) is in the range of 0.25 to 1.75 and at least a part of unreacted diamine in the reaction mixture is removed by distillation or extraction.

3. The amino composition according to claim 1, wherein the content of diamine represented by the following formula (1) is less than 2% by weight based upon the total weight of said amino composition.

4. A process for producing an amino composition according to claim 3, which comprises performing addition reaction of diamine represented by the formula (1) and styrene, wherein the reaction mole ratio of styrene and diamine (styrene/diamine) is in the range of 0.25 to 1.75 and at least a part of unreacted diamine in the reaction mixture is removed by distillation or extraction.

5. A curing agent for epoxy resin comprising the amino composition according to claim 3.

6. An epoxy resin composition comprising an epoxy resin and the curing agent for epoxy resin according to claim 5.

7. The epoxy resin composition according to claim 6, wherein said composition is used as a coating material.

8. An epoxy resin cured product obtained by curing the epoxy resin composition according to claim 7.

9. The epoxy resin composition according to claim 6, wherein said composition is used as a material for civil engineering and construction.

10. An epoxy resin cured product obtained by curing the epoxy resin composition according to claim 9.

11. An epoxy resin cured product obtained by curing the epoxy resin composition according to claim 6.

12. A curing agent for epoxy resin comprising the amino composition according to claim 1.

13. An epoxy resin composition comprising an epoxy resin and the curing agent for epoxy resin according to claim 12.

14. The epoxy resin composition according to claim 13, wherein said composition is used as a coating material.

15. An epoxy resin cured product obtained by curing the epoxy resin composition according to claim 14.

16. The epoxy resin composition according to claim 13, wherein said composition is used as a material for civil engineering and construction.

17. An epoxy resin cured product obtained by curing the epoxy resin composition according to claim 16.

18. An epoxy resin cured product obtained by curing the epoxy resin composition according to claim 13.

* * * * *